United States Patent [19]

Frey et al.

[11] 4,113,760

[45] Sep. 12, 1978

[54] PREPARATION OF ORGANOPOLYSILOXANE POLYMERS

[75] Inventors: Volker Frey; Rudolf Riedle; Peter John; Gerhard Kalchgruber, all of Burghausen; Helmut Spork, Altotting; Robert Leser, Burghausen, all of Germany

[73] Assignee: Wacker-Chemie GmbH, Munich, Germany

[21] Appl. No.: 808,767

[22] Filed: Jun. 22, 1977

[30] Foreign Application Priority Data

Jul. 8, 1976 [DE] Fed. Rep. of Germany ....... 2630744

[51] Int. Cl.$^2$ ................................................. C07F 7/08
[52] U.S. Cl. ............................................... 260/448.2 E
[58] Field of Search ................................. 260/448.2 E

[56] References Cited

U.S. PATENT DOCUMENTS

3,803,195   4/1974   Nitzsche et al. .............. 260/448.2 E

*Primary Examiner*—Paul F. Shaver

[57] ABSTRACT

An improved process for converting organopolysiloxane polymers which comprises reacting halosilanes which organopolysiloxanes in the presence of activated charcoal and if desired, an inorganic acid.

11 Claims, 1 Drawing Figure

PREPARATION OF ORGANOPOLYSILOXANE POLYMERS

BACKGROUND OF THE INVENTION

This invention relates to the preparation of organopolysiloxane polymers and more particularily to a process for preparing organopolysiloxane polymers by reacting halosilanes with organopolysiloxanes in the presence of activated charcoal.

Heretofore it was known that chlorosilanes and organosiloxanes undergo equlibrium reactions to form a mixture of compounds conprising some unreacted halosilanes and organopolysiloxanes. These reactions have been conducted in the presence of catalysts such as hydrogen halides, inorganic acids, Lewis acids, such as ferric chloride, alkali metal halides, inert polar solvents, amines, amine salts, ammonium salts and phosphorous compounds.

The equilibrium reactions of halogenosilanes with organosiloxanes in the presence of a catalyst such as a hydrogen halide or a mixture of a hydrogen halide or ferric chloride is well known as evidenced by the disclosure of U.S. Pat. No. 2,421,653 to Sauer.

Also U.S. Pat. No. 3,065,252 to Brown et al describes the reaction of halogenosilanes or halogenosiloxanes with organosiloxanes in the presence of catalysts, such as aminoalkyl-substituted organosilicon compounds, salts of monocarboxylic acids and aminoalkyl-substituted organosilicon compounds.

Brown et al describe in U.S. Pat. No. 3,101,361 the interaction of a silane or silicone containing at least one halogenated silicon atom per molecule with a siloxane in the presence of catalysts such as aliphatic hydrocarbon amines, salts of hydrogen halides and said amines and salts of monocarboxylic acid and aliphatic hydrocarbon amines and an organic solvent.

Also in U.S. Pat. No. 3,162,662 Brown et al describe a process for preparing linear chlorosiloxanes by interacting a halogenosilicon compound with cyclotrisiloxane in the presence of catalysts such as amines, amine salts of monocarboxylic acids, amine salts of monocarboxylic acids and quaternary ammonium halides, amides, alkali metal halides and ammonium salts of monocarboxylic acids and inert organic solvents.

Wegehaupt et al disclose in U.S. Pat. No. 3,549,680 a method for preparing organohalogenosilicon compounds by reacting halogenosilicon compounds with organosiloxanes free of halogen bonded silicon in the presence of phosphonitrile halides and certain organonitrogen derivatives of phosphorous acid or phosphoric acid.

Bennett describes in U.S. Pat. Nos. 3,642,851 and 3,686,253 a process for preparing linear halosiloxane polymers through the redistribution of halosiloxanes or a halosiloxane with cyclotrisiloxane or cyclotetrasiloxane in the presence of phosphine oxides or amine oxides.

U.S. Pat. No. 3,646,088 to Bakassian et al, discloses conducting the redistribution reaction between a siloxane and a chlorosilane in the presence of hexalkylphosphotriamide.

In comparison with the processes described above for conducting the equilibration reaction between organosiloxanes and chlorosilanes, the process of this invention has certain advantages. For example, it avoids cleavage of the SiC-bonded organic groups, such as phenyl, vinyl or gamma-chloropropyl groups and/or avoids the formation of decomposition products which have a noxious odor. Moreover, it does not require cyclotrisiloxanes which are relatively difficult to acquire, nor does it require considerable amounts of inert polar solvents which are expensive and often difficult to recover. Furthermore, the catalyst need not be separated from the reaction product nor is it necessary to neutralize the catalyst in the reaction product. Another advantage of the process of this invention is that there is a reduction in the reaction time with increased yields of product.

OBJECTS OF THE INVENTION

Therefore, it is an object of this invention to provide an improved process for equilibrating organosiloxanes. Another object of this invention is to provide an improved process for equilibrating organosiloxanes and halosilanes. Still another object of this invention is to provide an equilibration process which avoids cleavage of SiC-bonded organic groups. Still another object of this invention is to provide an equilibration process which does not require cyclotrisiloxanes. A further object of this invention is to provide an equilibration process which does not require inert polar solvents. A still further object of this invention is to provide an equilibration process which avoids neutralization and/or separation of the catalyst from the reaction product. Still a further object of this invention is to provide an equilibration process which provides increased yields of product with decreased reaction times.

SUMMARY OF THE INVENTION

The present invention relates to an improved process for equilibrating organosiloxanes which comprises reacting chlorosilanes with organosiloxanes in the presence of activated charcoal, either alone or in combination with an inorganic acid.

DETAILED DESCRIPTION OF THE INVENTION

Organosiloxanes which have been used heretofore or which could have been used in the known processes for equilibration of organosiloxanes and chlorosilanes can be employed as organosiloxanes in the process of this invention.

Preferred examples of organosiloxanes which may be employed in the process of this invention are cyclic siloxanes having the general formula:

$(R_2SiO)_n$, in which R represents hydrogen or the same or different monovalent hydrocarbon radicals and halogenated hydrocarbon radicals, with the provision that no more than one hydrogen atom may be bonded to each silicon atom; and $n$ is 3, 4, 5, 6, 7, 8, 9 or 10 and more preferably $n$ is 4, 5 or 6.

Examples of preferred linear organosiloxanes which may be employed in the process of this invention are those having the general formula:

$R_3SiO(R_2SiO)_mSiR_3$, in which R is the same as above and $m$ is 0 or a whole number The visocosity of the linear organosiloxanes is not critical; however, it is preferred that the viscosity not exceed about 25 cSt. at 25° C. Thus it is preferred that $m$ be a number of from 0 to 25.

The chlorosilanes employed in the process of this invention can be the same chlorosilanes which have been used or could have been used heretofore in previous processes for converting organosiloxanes by reacting with chlorosilanes. These chlorosilanes can be represented by the general formula:

$$R_xSiCl_{4-x}.$$

in which R is the same as above and $x$ is 0, 1, 2 or 3.

In the preferred embodiment of the process of this invention the organosiloxanes which are to be converted are those represented by the following general formula:

$$R_3SiO(R_2SiO)_mSiR_3,$$

$m$ is preferably 0, 1 or 2.

Examples of monovalent hydrocarbon radicals represented by R are straight chain or branched chain aliphatic hydrocarbon radicals, such as alkyl radicals; e.g., the methyl, ethyl, isopropyl, sec.-butyl and 2-ethylhexyl radical, as well as dodecyl, octadecyl and eicosyl radicals; alkenyl radicals, such as the vinyl radical and the allyl radical as well as hexadienyl radicals; cycloalkyl radicals, such as the cyclopentyl an cyclohexyl radicals; cycloalkenyl radicals, such as cyclopentenyl and cyclohexenyl radicals aryl radicals, such as the phenyl radical as well as naphthyl and xenyl radicals; aralkyl radicals, such as the benzyl and phenylethyl radicals; and alkaryl radicals such as the tolyl and dimethylphenyl radicals. Examples of halogenated monovalent hydrocarbon radicals are the 3-chloropropyl radical, the 3,3,3-trifluoropropyl radical, the 3,3,4,4,5,5,5-heptafluoropentyl radical, the 2,4,6-trichlorobenzyl radical, the perchlorophenyl-2-bromonaphtyl radical, the p-iodophenylethyl radical and the p-fluorophenyl radical.

It is however preferred that a methyl radical be bonded to each of the silicon atoms in the cyclosiloxanes in accordance with the general formula:

$$(R_2SiO)_n.$$

Moreover it is preferred that the organic radicals R in the chlorosilanes have a maximum of about 6 carbon atoms.

Because of its availability, octamethylcyclotetrasiloxane is the preferred cyclosiloxane.

Organosiloxanes which may be employed in this invention are those having the general formula:

$$R_3SiO(R_2SiO)_mSiR_3$$

in which R and $m$ are the same as above. Suitable examples of these organosiloxanes are hexamethyldisiloxane, 1,1,3,3-tetramethyldisiloxane, octamethyltrisiloxane, decamethyltetrasiloxane, 1,1,3,3,5,5-hexamethyltrisiloxane, 3-phenylheptamethyltrisiloxane, 1,3-divinyltetramethyldisiloxane, 1,1,1,5,5,5-hexamethyl-3,3-diphenyltrisiloxane, 1,1,5,5-tetramethyl-3,3-diphenyltrisiloxane; dimethylpolysiloxanes having trimethylsiloxy terminal groups and dimethylpolysiloxanes having dimethylhydrogensiloxy terminal groups.

Mixtures of various organosiloxanes may also be employed in the process of this invention.

Examples of silanes having the general formula:

$$R_xSiCl_{4-x}$$

are methyltrichlorosilane, dimethyldichlorosilane, vinyl-trichlorosilane, tetrachlorosilane, phenyltrichlorosilane, diphenyldichlorosilane and methylvinyldichlorosilane. Mixtures of various chlorosilanes may also be employed in the process of this invention.

It is preferred that the chlorosilane be used in an amount of from 1 to 10 mols per mol of cyclosiloxane or from 1 to 10 mols per gram atom of hydrogen present in the grouping $R_3SiO$ in linear organosiloxanes having the general formula:

$$R_3SiO(R_2SiO)_mSiR_3.$$

Surprisingly, when cyclosiloxanes are used in the process of this invention, the resultant mixture does not consist exclusively of linear siloxanes which have the same number of Si-atoms in the chain as the cyclosiloxanes employed, nor a multiple of that number of Si-atoms. This is in direct contrast with the equation illustrated in U.S. Pat. No. 3,101,361, which describes the reaction of a cyclosiloxane with a chlorosilane. When cyclosiloxanes are employed as the organosiloxanes in the process of this invention, a mixture of linear organosiloxanes having the general formula:

$$Cl(R_2SiO)_ySiR_xCl_{3-x},$$

are obtained, wherein $y$ is a number with a value of from 1 to 11. This shows that when cyclosiloxanes are used in the process of this invention, the following reactions occur, (1) $R_xSiCl_{4-x} + (R_2SiO)_n \rightarrow Cl(R_2SiO)_nSiR_xCl_{3-x}$, (2) $nR_xSiCl_{4-x} + (R_2SiO)_n \rightarrow nClR_2SiOSiR_xCl_{3-x}$ However when $x$ has a value of 1, other organosiloxanes or organopolysiloxanes having Si-bonded chlorine can be formed.

The nearer the amount of chlorosilane approximates 1 mol per mol of cyclosiloxane, the more the reaction is favored in accordance with that shown in equation (1) above. As the amount of chlorosilane exceeds the 1 mol for each mol of cyclosiloxane, the more the reaction is favored in accordance with that shown in equation (2) above.

When organosiloxanes having the general formula:

$$R_3SiO(R_2SiO)_mSiR_3$$

are reacted with silanes of the general formula:

$$R_{x'}SiCl_{4-x'}$$

where $x'$ is 0, 1 or 2, silanes of the general formula:

$$R_3SiCl$$

and chlorosilanes having the general formula:

$$R_{x'}SiCl_{3-x'}O(SiR_2O(JSiR_2O)_mSiR_{x'}Cl_{3-x'}$$

and/or $$R_{x'}SiCl_{3-x'}OSiR_{x'}Cl_{2-x'}O)(SiR_2O)_mSiR_{x'}Cl_{3-x'}$$

are obtained. Likewise, when disiloxanes ($m = 0$) are used as the organosiloxanes, it is possible to obtain silanes having the general formula:

$$R_3SiCl$$

and organosiloxanes corresponding to the general formula:

$$R_3Si(OSiR_2)_{m'}OSiR_3,$$

$$R_3Si(O\underset{\underset{\underset{SiR_3}{|}}{\underset{|}{O}}}{\overset{|}{Si}})_{m'}OSiR_3 \text{ and}$$

$$R_3Si(O\underset{\underset{\underset{SiR_3}{|}}{\underset{|}{O}}}{\overset{\overset{\overset{SiR_3}{|}}{\overset{|}{O}}}{SiO}})_{m'}OSiR_3,$$

where $m'$ represents a number of from 1 to 6.

The amount of activated charcoal which is employed as a catalyst, is preferably from about 0.1 to 30 percent by weight and more preferably from 0.5 to 15 percent by weight, based on the total weight of the reactants present in the reaction vessel.

When the charcoal employed has not been activated by an acid, for example so-called phosphoric acid coal, then an inorganic acid is preferably employed in the process of this invention. Suitable examples of inorganic acids which may be employed are hydrogen chloride, sulfuric acid and phosphoric acid. Anhydrous hydrogen chloride can be produced in situ by reacting the chlorosilane with a small amount of water, for example 0.0001 to 1 percent by weight based on the weight of the organosiloxanes, which may be present in the organosiloxanes or it may be absorbed in the activated charcoal. Hydrogen chloride may also be passed through the mixture of reaction components. When a liquid inorganic acid is used at room temperature and at 760 mm Hg (abs.), it is preferred that the liquid inorganic acid be employed in an amount of from 0.1 to 5 percent by weight based on the weight of the activated charcoal and that it be absorbed by the activated charcoal.

If desired, the process of this invention can be carried out in the presence of a solvent which is inert to the reactants. Examples of suitable inert solvents are hydrocarbons and halogenated hydrocarbons which are liquid at room temperature and at 760 mm Hg (abs.), such as benzene, toluene, xylene, ligroin, methylene chloride, perchloroethylene and chlorobenzene. It is however preferred that none of the compounds contain hydroxyl groups except that traces of Si-bonded hydroxyl groups may be present in the organosiloxanes as impurities. Traces of hydroxyl groups may also be present in the inorganic acids or on the surfaces of the activated charcoal.

The process is preferably carried out at atmospheric pressure, i.e. at 760 mm Hg (abs.) or at approximately 760 mm Hg (abs.). However if desired or necessary, the process may also be carried out under increased pressures, such as for example from 1.1 to 5.0 bar, as might be required in order to overcome the pressure of the liquid column, such as, for example when chlorosilane or hydrogen chloride are introduced into the reaction chamber; or the process can be carried out at subatmospheric pressure, for example at 0.05 to 0.99 bar, as might be desirable in order to operate at a relatively low temperature.

The process is preferably carried out at temperatures between room temperature and 200° C, and particularly at the reflux temperature of at least one of the reaction components and/or reaction products.

The process can be carried out batch-wise, semicontinuously or continuously.

The reaction mixture can be stirred or agitated in order to assure a good dispersion of the various components.

Preferably, when a linear organosiloxane is to be reacted with chlorosilane as a continuous process, in a reaction column equipped with a fractionating device, the chlorosilane is introduced into the top stratum of the activated charcoal in the column, while the organosiloxane having the general formula:

$$R_3SiO(R_2SiO)_{m''}SiR_3,$$

where R is the same as above and $m''$ is 0, 1 or 2, is introduced at the bottom or below the activated charcoal stratum. Also, when the organosiloxane has the general formula:

$$R_3SiO(R_2SiO)_{m'''}SiR_3,$$

where R is the same as above and $m'''$ is 0 or a number having a value of from 1 to 25, then it is preferably introduced into the top of the activated charcoal stratum and the chlorosilane is introduced at the lower end of or below the activated charcoal stratum and then the mixture of reaction components and reaction products in the reaction column are heated to ebullition. Metering of the siloxane or chlorosilane introduced at the bottom or below the activated charcoal stratum is regulated by means of a device which is controlled by the temperature which prevails in the lower third of the reaction column.

A preferred embodiment of the process of this invention is illustrated by the accompanying diagram which illustrates the manner in which the present invention can be practiced.

Figure 1:
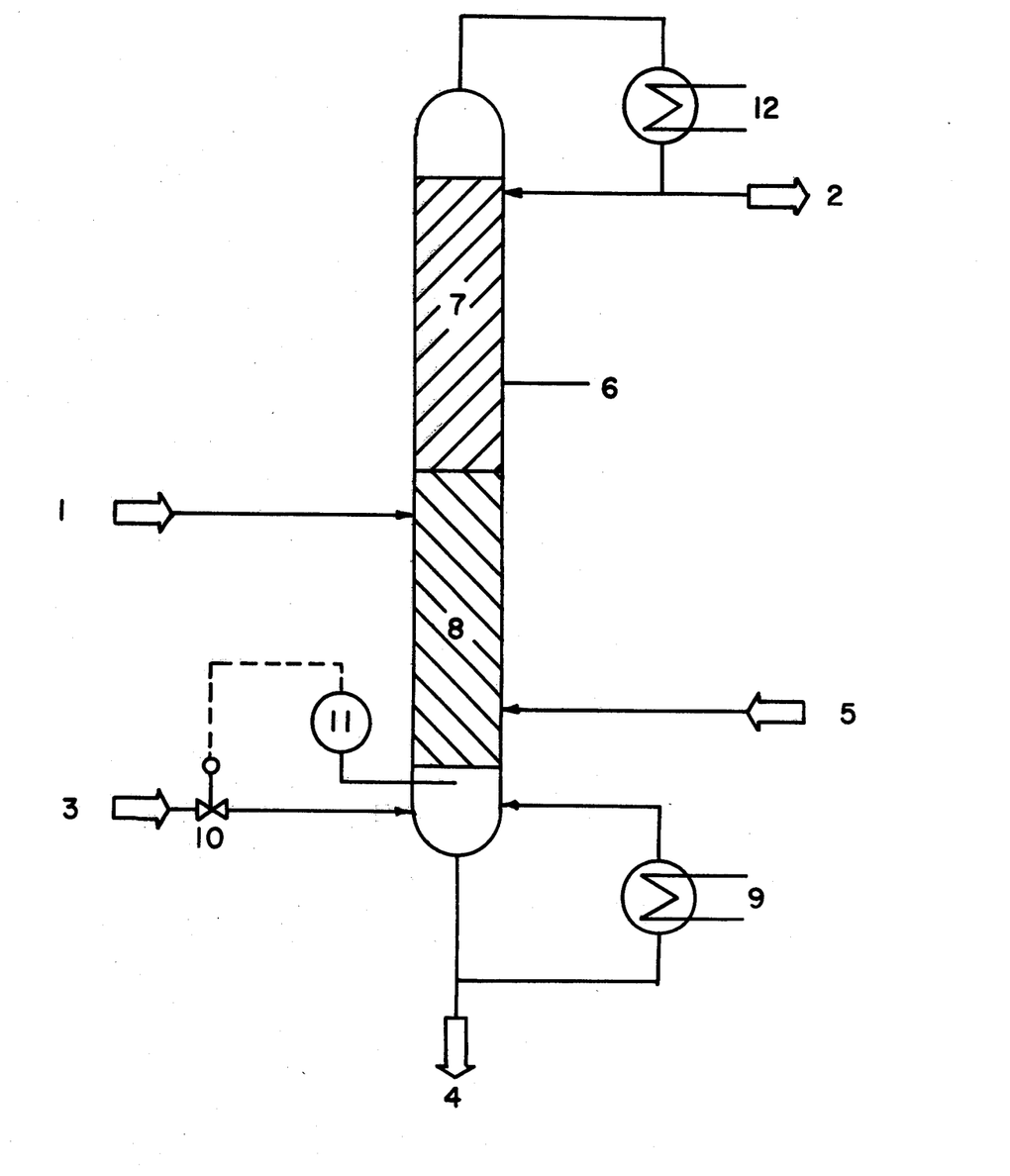

Referring specifically to the accompanying drawing, and using disiloxanes as an example of an organosiloxane, a liquid chlorosilane having the general formula:

$$R_xSiCl_{4-x}$$

is continuously introduced into the reaction column 6 through a conduit 1. The lower half or up to two-thirds of the reaction column is filled with commercially available granulated activated charcoal 8. The upper one-third of the reaction tower serves as a fractionating device 7 and is filled with saddle-shaped packing (Berl saddies), Raschig rings or so-called "Pallrings". (The term "Pallring" is a registered trademark). By means of a metering device 10 such as for example a metering pump, a disiloxane is introduced into the reaction column 6 through conduit 3. In the reaction column the disiloxane is heated to ebullition by a forced circulation evaporator 9 before the chlorosilane is introduced into the reaction column. The distance between conduit 1 and conduit 3 is preferably at least 1.50 meter, however, the upper limit for the distance is not critical. Within the lower one-third of reaction column 6 is mounted a thermocouple which, through control element 11 engages the metering apparatus 10. When the temperature exceeds by 40° to 80° C the boiling point of the disiloxanes in the column at the applicable operating pressure, and when the temperature drops below the indicated range it shuts off the metering apparatus 10. The temperature range is selected so that the product exiting through conduit 4 contains from 0.1 to 20 percent by weight based on the weight of the disiloxanes used as starting material.

Gaseous hydrogen chloride, preferably in an amount of from 0.1 to 50 liters (as measured at 0° C and 760 mm Hg (abs.) per liter of disiloxane in column 6 is conveyed to reaction column 6 through conduit 5. The organosilane having the general formula $R_3SiCl$ exiting through the top of reaction column 6 is condensed in cooler 12. The silane is partially recirculated as return flow for the fractionation of the compounds in the packing material stratum 7 and partially withdrawn through conduit 2.

The organopolysiloxanes corresponding to the following formula:

where $m'$ represents a number having a value of 1 to 6, which have been obtained from the reaction of a chlorosilane with a disiloxane are withdrawn through conduit 4 with the aid of a device (not illustrated in the drawing) which assures that the contents of the forced circulation evaporator 9 remain at a constant level.

When an excess of chlorosilane from conduit 1 is used, the product exiting from conduit 4 may, for example also contain siloxanes corresponding to the formula $RSiCl_2OSiR_3$. Such siloxanes can be used for the preparation of valuable modified siloxanes.

When it is desired to obtain primarily organopolysiloxanes having the following formula:

then they can be easily separated from the mixture exiting through conduit 4 by distillation. The residue obtained from the distillation can be recirculated to reaction column 6 together with chlorosilane through conduit 1.

When a disiloxane is added through conduit 1 and a chlorosilane having the formula $R_x SiCl_{4-x'}$ is introduced through conduit 3 to reaction column 6, quite surprisingly, conduit 4 does not yield organopolysiloxanes free of chlorine as indicated by the previous formulas, but rather yields siloxanes corresponding to the following general formula:

in which R and $x'$ are the same as above and $y'$ is a number having a value of from 1 to 5.

The organopolysiloxanes formed from the reaction of the chlorosilane and disiloxane are especially valuable as components in the preparation of polyurethane foams, as well as for example as polishing agents or as components of polishing agents, as damping oils and as diffusion pump oils.

The organosiloxanes or the organopolysiloxanes containing Si-bonded chlorine which are obtained as the result of the various embodiments of the process of this invention can be converted, for example by hydrolysis, into organopolysiloxanes whose siloxane units have a predetermined structure at least within a certain range; for example siloxane units whose vinylmethylsiloxane units alternate with a predetermined number of dimethylsiloxane units. Also these organosiloxanes or organopolysiloxanes may be converted into organosiloxanes or organopolysiloxanes having terminal amino groups by reacting these siloxanes with ammonia or amines; or they may be converted into organosiloxanes or organopolysiloxanes having terminal hydrocarbonoxy groups by reacting the siloxanes with hydrocarbons which contain hydroxyl groups. These chlorine-containing organosilicon compounds can of course also be used in the Grignard synthesis or in reactions with cyclic organopolysiloxanes.

In addition to the recovery of, for example, trimethylchlorosilane from hexamethyldisiloxane obtained as a byproduct during the silylization processes, the process of this invention also provides a method for purifying silanes, especially silanes containing Si-bonded hydrogen which are contaminated with organic compounds. The silanes which are to be purified are hydrolyzed and the hydrolysates distilled and once more converted into silanes in accordance with the process of this invention.

In the following examples the activated charcoal employed is the "EKT IV" type (Vendor: Lurgi-Apparate-Technit, Frankfort/Main, BRD), which is granulated and has a diameter of approximately 4mm. Prior to use it is heated in a drying chamber for 10 hours at 200° C.

The quantities of gas indicated in the following examples are determined at 0° C and at 760 mm Hg (abs.) unless otherwise specified.

EXAMPLE 1

A mixture consisting of 17 grams of activated charcoal, 2 mols of octamethylcyclotetrasiloxane and 3 mols of dimethyldichlorosilane is heated for 20 hours to ebullition under reflux in a flask which is equipped with a reflux condenser and a thermometer. The temperature of the flask's contents increases from 82° C to 119° C. The flask's contents are then cooled, filtered and the filtrate analyzed by gas chromatography. The results are illustrated in Table I.

TABLE 1

| Components | Percent |
|---|---|
| $(CH_3)_2SiCl_2$ | 12.6 |
| $Cl(CH_3)_2SiOSi(CH_3)_2Cl$ | 9.6 |
| $Cl[(CH_3)_2SiO]_2Si(CH_3)_2Cl$ | 9.2 |
| $Cl[(CH_3)_2SiO]_3Si(CH_3)_2Cl$ | 7.3 |
| $Cl[(CH_3)_2SiO]_4Si(CH_3)_2Cl$ | 31.9 |
| $Cl[(CH_3)_2SiO]_5Si(CH_3)_2Cl$ | 1.8 |
| $Cl[(CH_3)_2SiO]_6Si(CH_3)_2Cl$ | 0.4 |
| $Cl[(CH_3)_2SiO]_7Si(CH_3)_2Cl$ | 0.1 |
| $[(CH_3)_2SiO]_3$ | 0.3 |
| $[(CH_3)_2SiO]_4$ | 22.7 |
| $[(CH_3)_2SiO]_5$ | 1.6 |
| $[(CH_3)_2SiO]_6$ | 1.5 |
| $[(CH_3)_2SiO]_7$ | 0.5 |
| $[(CH_3)_2SiO]_8$ | 0.3 |

EXAMPLE 2

A mixture consisting of 50 grams of activated charcoal, 6 mols of octamethylcyclotetrasiloxane and 9 mols of dimethyldichlorosilane are added to a flask equipped with a reflux condenser, a thermometer and a gas dispersing pipe connected on its lower end in the flask to a glass sinter plate. About 10 liters per hour of gaseous hydrogen chloride is conveyed through the flask in which the mixture is heated for 11 hours to ebullition under reflux. The temperature of the contents in the flask increases from 82° C to 150° C.

The contents of the flask are cooled, filtered and the filtrate analyzed by gas chromatography. The results are illustrated in Table 2.

TABLE 2

| Components | Percent |
|---|---|
| $(CH_3)_2SiCl_2$ | 3.8 |
| $Cl(CH_3)_2SiOSi(CH_3)_2Cl$ | 18.1 |
| $Cl[(CH_3)_2SiO]_2Si(CH_3)_2Cl$ | 20.5 |
| $Cl[(CH_3)_2SiO]_3Si(CH_3)_2Cl$ | 16.7 |
| $Cl[(CH_3)_2SiO]_4Si(CH_3)_2Cl$ | 27.1 |
| $Cl[(CH_3)_2SiO]_5Si(CH_3)_2Cl$ | 5.3 |
| $Cl[(CH_3)_2SiO]_6Si(CH_3)_2Cl$ | 1.5 |
| $Cl[(CH_3)_2SiO]_7Si(CH_3)_2Cl$ | 0.6 |
| $[(CH_3)_2SiO]_4$ | 3.8 |
| $[(CH_3)_2SiO]_5$ | 1.1 |
| $[(CH_3)_2SiO]_6$ | 0.8 |
| $[(CH_3)_2SiO]_7$ | 0.4 |
| $[(CH_3)_2SiO]_8$ | Trace |

EXAMPLE 3

The process described in Example 2 is repeated, except that the filtrate is fractionally distilled at normal atmospheric pressure. About 117 grams (4 percent by weight based on the total weight of the organosilicon compounds employed) of dimethyldichlorosilane are obtained at 71° C. About 528 grams (18 percent by weight based on the total weight of the organosilicon compounds) of 1,3-dichlorotetramethyldisiloxane are obtained at a temperature between 135° and 138° C.

The distillation residue is again mixed with 9 mols of dimethyldichlorosilane and 50 grams of activated charcoal and heated to ebullition under reflux while 10 liters per hour of gaseous hydrogen chloride are passed through the contents of the flask. The filtrate is then fractionally distilled. When the distillation residue is heated in the presence of activated charcoal and hydrogen chloride and the filtration and fractional distillation of the filtrate is repeated 5 times, a total of 2408 grams of dichlorotetramethyldisiloxane is obtained.

EXAMPLE 4

A mixture containing 17 grams of activated charcoal, 1 mol vinylheptamethylcyclotetrasiloxane and 1.5 mols of dimethylchlorosilane is placed in a flask which is equipped with a gas dispersing tube connected on its lower end in the flask to a glass sinter plate, a reflux condenser and a thermometer. About 5 liters per hour of gaseous hydrogen chloride are passed through the mixture while heating to ebullition under reflux over a period of 5 hours. The temperature of the flask's contents increases from 82° to 150° C. The contents are cooled, filtered and the filtrate analyzed by gas chromatography. The results are shown in Table 3.

TABLE 3

| Components | Percent |
|---|---|
| Dimethyldichlorosilane | 9.2 |
| Vinylmethyldichlorosilane | 2.9 |
| 1,3-Dichlorotetramethyldisiloxane | 4.7 |
| 1,3-Dichloro-1-vinyltrimethyldisiloxane | 6.8 |
| 1,5-Dichlorohexamethyltrisiloxane | 2.2 |
| 1,5-Dichlorovinylpentamethyltrisiloxane | 4.8 |
| 1,7-Dichlorooctamethyltetrasiloxane | 2.6 |
| 1,7-Dichlorovinylheptamethyltetrasiloxane | 5.3 |
| 1,9-Dichlorodecamethylpentasiloxane | 6.5 |
| 1,9-Dichlorovinylnonamethylpentasiloxane | 39.9 |
| 1,11-Dichloroodecylmethylhexasiloxane | 4.5 |
| 1,11-Dichlorovinylundecylmethylhexasiloxane | 5.3 |
| 1,13-Dichlorotetradecylmethylheptasiloxane | 2.8 |
| 1,13-Dichlorovinyltridecylmethylheptasiloxane | 0.4 |
| Vinylheptamethylcyclotetrasiloxane | 1.5 |
| $[(CH_3)_2SiO]_4$ | trace |
| $[(CH_3)_2SiO]_5$ | trace |
| 1,3-Dichloro-1,3-divinyldimethyldisiloxane | trace |

EXAMPLE 5

A mixture consisting of 17 grams of activated charcoal, 1 mol of octamethylcyclotetrasiloxane and 1.5 mols of vinylmethyldichlorosilane is placed in a flask similar to that described in Example 4. About 3 liters per hour of gaseous hydrogen chloride are passed through the mixture while it is heated to ebullition under reflux until the temperature of the flask's contents reaches 150° C. The contents are cooled and filtered. The filtrate consists of a mixture of organosiloxanes having the formula:

$$Cl[(CH_3)_2SiO]_aSi(CH_3)_2Cl,$$

in which $a$ represents 0, 1, 2 or 3; and organosiloxanes of the formula:

$$Cl[(CH_3)_2SiO]_bSi(CH_3)(C_2H_3)Cl,$$

where $b$ is 0, 1, 2, 3 or 4. Also the filtrate contains about 1.7 percent by weight of octamethylcyclotetrasiloxane based on the weight of octamethylcyclotetrasiloxane employed.

EXAMPLE 6

Methyltrichlorosilane is heated to ebullition under reflux in a 2-meter long column which has a diameter of 50 millimeters and which is filled with activated charcoal and equipped with a forced circulation evaporator. About 5 liters per hour of gaseous hydrogen chloride are introduced at the bottom of the column, while 1.64 mols of octamethylcyclotetrasiloxane is introduced through the top of the column. After the temperature in the forced circulation evaporator has reached 155° C, 2.38 mols of methyltrichlorosilane is pumped through the bottom of the column in addition to hydrogen chloride, so that the temperature in the forced circulation evaporator remains constant at 155° C. A mixture of organosilicon compounds is drawn off through a side arm. Table 4 shows the contents of the mixture in percent as determined by the gas chromatogram.

TABLE 4

| Contents | Percent (Approximate) |
|---|---|
| $CH_3SiCl_3$ | 3 |
| $[Cl_l(CH_3)_{3-l}Si]_2O$ | 20 |
| $Cl_l(CH_3)_{3-l}SiOSi(CH_3)_{2-p}Cl_pOSi(CH_3)_{3-l}Cl_l$ | 27 |
| $Cl_l(CH_3)_{3-l}Si[OSi(CH_3)_{2-p}Cl_p]_2OSi(CH_3)_{3-l}Cl_l$ | 15 |
| $Cl_l(CH_3)_{3-l}Si[OSi(CH_3)_{2-p}Cl_p]_3OSi(CH_3)_{3-l}Cl_l$ | 22 |
| $Cl_l(CH_3)_{3-l}Si[OSi(CH_3)_{2-p}Cl_p]_4OSi(CH_3)_{3-l}Cl_l$ | 6 |
| $[(CH_3)_2SiO]_4$ | 4 |
| Higher chlorosiloxanes | trace |

$l = 1$ or 2; $p = 0$ or 1

EXAMPLE 7

Dimethyldichlorosilanes are heated to ebullition under reflux in a 2 meter long column having a diameter of 50 millimeters which is filled with activated charcoal and which is equipped with a forced circulation evaporator. About 5 liters of gaseous hydrogen chloride are introduced through the bottom of the column, while 690 milliliters perhour of a mixture consisting of:

1.5 percent by weight of hexamethylcyclotrisiloxane, 76.5 percent by weight of octamethylcyclotetrasiloxane, 18 percent by weight of decamethylcyclopentasiloxane, and 4 percent by weight of dodecamethylcyclohexasiloxane are introduced through the top of the column. After the forced circulation evaporator has attained a temperature of from 150 to 155° C, 327 milliliters of dimethyldichlorosilane per hour are introduced at the bottom of the column in addition to the hydrogen chloride in order to maintain a constant temperature in the forced circulation evaporator. A mixture of organosilicon compounds is withdrawn through a side arm. Table 5 shows the contents of the mixture in percent, as determined by the gas chromatogram.

TABLE 5

| Contents | Percent |
|---|---|
| $(CH_3)_2SiCl_2$ | 7.8 |
| $Cl(CH_3)_2SiOSi(CH_3)_2Cl$ | 27.7 |
| $Cl[(CH_3)_2SiO]_2Si(CH_3)_2Cl$ | 15.0 |
| $Cl[(CH_3)_2SiO]_3Si(CH_3)_2Cl$ | 9.2 |
| $Cl[(CH_3)_2SiO]_4Si(CH_3)_2Cl$ | 22.3 |
| $Cl[(CH_3)_2SiO]_5Si(CH_3)_2Cl$ | 6.5 |
| $Cl[(CH_3)_2SiO]_6Si(CH_3)_2Cl$ | 1.4 |
| $Cl[(CH_3)_2SiO]_7Si(CH_3)_2Cl$ | 0.5 |
| $[(CH_3)_2SiO]_3$ | 0 |
| $[(CH_3)_2SiO]_4$ | 5.9 |
| $[(CH_3)_2SiO]_5$ | 3.0 |
| $[(CH_3)_2SiO]_6$ | 0.5 |
| $[(CH_3)_2SiO]_7$ | 0 |
| $[(CH_3)_2SiO]_8$ | 0 |

EXAMPLE 8

About 50 grams of activated charcoal, 1 mol (162 grams) of hexamethyldisiloxane and 4 mols (516 grams) of dimethyldichlorosilane are heated in a flask which is equipped with a thermometer and a fractional distillation device as well as a conduit for the introduction of gas which terminates inside the flask with a glass sinter plate. The mixture is heated to ebullition while 3 liters per hour of gaseous hydrogen chloride are passed through. As soon as the temperature at the top of the fractional distillation column is between 57.5° and 58° C, trimethylchlorosilane is distilled off while the aforementioned temperature remains constant. However the temperature of the flask's contents increases from 73° C to 98° C.

About 222 grams of trimethylchlorosilane having a purity of 97 percent by weight (3 percent by weight dimethyldichlorosilane) are obtained, i.e. almost 100 percent of theoretical.

Analysis by gas chromatography shows that the distillation residue contains organosiloxanes corresponding to the following formula:

$$ClSi(CH_3)_2O[Si(CH_3)_2O]_cSi(CH_3)_2Cl,$$

in which $c$ is 0, 1, 2, 3, 4, 5, 6 or 7 and where siloxanes with $c$ values of 0, 1 or 2 constitute a majority of the components, in addition to traces of cyclic siloxanes of the formula:

$$[(CH_3)_2SiO]_d,$$

in which formula $d$ is 4 or 5; and excess dimethyldichlorosilane.

EXAMPLE 9

The process described in Example 8 is repeated, except that 4 mols (598 grams) of methyltrichlorosilane are used instead of dimethyldichlorosilane.

About 224 grams of trimethylchlorosilane having a purity of 97 percent by weight (3 percent by weight of methyltrichlorosilane) are obtained, i.e. essentially 100 percent of theoretical.

Analysis by gas chromatography indicates that the distillation residue contains organosiloxanes of the following formula:

$$Cl_2SiCH_3[OSiCl(CH_3)]_eOSi(CH_3)Cl_2,$$

where $e$ is 0, 1, 2 or 3, in addition to traces of cyclic siloxanes of the following formula:

$$[(CH_3)ClSiO]_d,$$

where $d$ is 4 or 5; and excess methyltrichlorosilane.

EXAMPLE 10

About 50 grams of activated charcoal, 1 mol (134 grams) tetramethyldisiloxane and 4 mols (516 grams) dimethyldichlorosilane are placed in a flask equipped in accordance with Example 8. The mixture is heated to ebullition while 3 liters per hour of gaseous hydrogen chloride are passed through. As soon as a temperature of 35° C has been attained at the top of the fractional distillation column, dimethylchlorosilane is distilled off while the cited temperature remains constant. However, the temperature of the flask's contents increases from 63° C to 98° C.

Approximately 187.5 grams of dimethylchlorosilane having a purity of 96 percent by weight (4 percent by weight of dimethyldichlorosilane) are obtained, i.e., 95.2 percent of theoretical.

Analysis by gas chromatography indicates that the distillation residue contains organosiloxanes corresponding to the formula:

$$ClSi(CH_3)_2O[Si(CH_3)_2O]_fSi(CH_3)_2Cl$$

where $f$ is 0, 1, 2, 3, 4, 5 or 6. Siloxanes having $f$ values of 0, 1 or 2 form the majority of the components, in addition to traces of cyclic siloxanes of formula:

$$[(CH_3)_2SiO]_d,$$

in which $d$ is 4 or 5.

EXAMPLE 11

The process described in Example 10 is repeated, except that 4 mols (598 grams) of methyltrichlorosilane are substituted for the dimethyldichlorosilane.

About 187 grams of dimethylchlorosilane having a purity of 96.2 percent by weight (3.8 percent by weight of methyltrichlorosilane) are obtained, which is about 95 percent of theoretical.

Analysis by gas chromatography indicates that the distillation residue contains organosiloxanes corresponding to the formula:

$$Cl_2SiCH_3[OSiCl(CH_3)]_eOSi(CH_3)Cl_2,$$

where $e$ is 0, 1, 2, or 3, in addition to traces of siloxanes of the formula:

$$Cl[Si(CH_3)_2O]_gSi(CH_3)_2Cl,$$

where $g$ is 2 or 3.

EXAMPLE 12

The process described in Example 8 is repeated, except that 1 mol (236 grams) of octamethyltrisiloxane is substituted for the hexamethyldisiloxane.

About 224 grams of trimethylchlorosilane having a purity of 97 percent by weight (3 percent by weight of dimethyldichlorosilane) are obtained, i.e., essentially 100 percent of theoretical.

The gas chromatogram indicates that the distillation residue contains organosiloxanes of the formula:

$$ClSi(CH_3)_2O[Si(CH_3)_2O]_cSi(CH_3)_2Cl$$

in which $c$ is 0, 1, 2, 3, 4, 5, 6 or 7. Siloxanes having $c$ values of 1 or 2 are the principal components, in addition to traces of cyclic siloxanes of the formula:

$$[(CH_3)_2SiO]_d$$

where $d$ is 4 or 5.

EXAMPLE 13

The process described in Example 8 is repeated, except that 4 mols (564.4 grams) vinylmethyldichlorosilane are substituted for the dimethyldichlorosilane.

Approximately 219 grams of trimethylchlorosilane are obtained, i.e. essentially 100 percent of theoretical.

The gas chromatogram indicates that the distillation residue contains organosiloxanes of the formula:

$$ClSi(CH_3)(C_2H_3)O[Si(CH_3)(C_2H_3)O]_eSi(CH_3)(C_2H_3)Cl$$

where $e$ is 0, 1, 2 or 3. Siloxanes having an $e$ value of 0 and 1 are the principal constituents, in addition to excess vinylmethyldichlorosilane.

EXAMPLE 14

About 50 grams of activated charcoal, 500 grams of dimethyldichlorosilane and 500 grams of organopolysiloxane comprising 86.4 percent by weight of dimethylsiloxane units and 13.6 percent by weight of trimethylsiloxane units and having a viscosity of 10 cSt. at 25° C are placed in a flask which is equipped in accordance with Example 8. The mixture is heated to ebullition while 4 liters per hour of gaseous hydrogen chloride are passed through the contents of the flask. As soon as the temperature at the top of the fractional distillation column reaches 57° C, trimethylchlorosilane is distilled off, while the temperature remains constant.

About 104 grams of trimethylchlorosilane having a purity of 97 percent by weight (3 percent by weight of dimethyldichlorosilane) are obtained which is about 100 percent of theoretical.

The distillation residue consists primarily of organosiloxanes corresponding to the formula:

$$ClSi(CH_3)_2O[Si(CH_3)_2O]_hSi(CH_3)_2Cl$$

where $h$ is 0 or where $h$ is a whole number having a value of from 1 to 11, in addition to traces of cyclic siloxanes of the formula:

$$[(CH_3)_2SiO]_{d'}$$

where $d'$ is 4, 5, 6, 7 or 8.

EXAMPLE 15

The reaction column 6 has a length of 2.80 meters and a diameter of 50 millimetrers. In the tower, a layer of activated charcoal 8 extends from 30 millimeters above the tower's lower end up to 1.80 meters above the reaction column's lower end. Above the layer of activated charcoal is a layer of Raschig rings having a diameter of 5 millimeters 7. The forced circulation evaporator 9 is filled with hexamethyldisiloxane which is heated to ebullition under reflux. Dimethyldichlorosilane is then introduced through conduit 1 and gaseous hydrogen chloride is introduced through conduit 5 to reaction column 6, until a temperature of 150° C is attained at the temperature sensing device which is connected to the control element 11. The trimethylchlorosilane formed is removed from condenser 12 through conduit 2 via an automatic fractional separator (not illustrated) which is controlled so that the temperature does not exceed 57.6° C at the top of column 6.

After the previously mentioned temperature has been attained by the temperature sensing device which is connected to the control element 11, 1.03 mols per hour of dimethyldichlorosilane are pumped into the reaction column 6 through conduit 1 with the flow being regulated by the control element 11 via a pump 10; while 1.72 mols of hexamethyldisiloxane per hour is introduced through conduit 3 and 3 liters per hour of gaseous hydrogen chloride are pumped into the reaction column 6 through conduit 5. By switching the pump 10 on and off, the control element 11 maintains a constant temperature of 150° ± 2° C.

An hourly average of 2.05 mols of trimethylchlorosilane, which is essentially 100 percent of theoretical, is obtained through conduit 2.

The following Table 6 shows the distribution of the product in percent exiting through conduit 4, as determined by the gas chromatogram.

TABLE 6

| Components | Percent |
|---|---|
| $(CH_3)_3SiOSi(CH_3)_3$ | 13.9 |
| $(CH_3)_3SiOSi(CH_3)_2OSi(CH_3)_3$ | 50.1 |
| $(CH_3)_3SiO[Si(CH_3)_2O]_2Si(CH_3)_3$ | 22.8 |
| $(CH_3)_3SiO[Si(CH_3)_2O]_3Si(CH_3)_3$ | 7.9 |
| $(CH_3)_3SiO[Si(CH_3)_2O]_4Si(CH_3)_3$ | 2.8 |
| $(CH_3)_3SiO[Si(CH_3)_2O]_5Si(CH_3)_3$ | 1.1 |
| $(CH_3)_3SiO[Si(CH_3)_2O]_6Si(CH_3)_3$ | 0.5 |
| $(CH_3)_3SiO[Si(CH_3)_2O]_7Si(CH_3)_3$ | 0.2 |
| $Cl(CH_3)_2SiOSi(CH_3)_2Cl$ | 0.5 |
| $Cl(CH_3)_2SiO[Si(CH_3)_2O]_2Si(CH_3)_2Cl$ | 0.2 |

EXAMPLE 16

Dimethyldichlorosilane is introduced into the forced circulation evaporator 9 of reaction column 6 described in Example 15 which contains activated charcoal and Raschig rings. The dimethyldichlorosilane is heated to ebullition under reflux. Thereafter hexamethyldisiloxane is passed through conduit 1 and gaseous hydrogen chloride is introduced through conduit 5 into reaction column 6. The temperature sensing device which is connected with the control element 11 senses a temperature between 150° and 155° C. The trimethylchlorosilane formed is withdrawn through conduit 2 via the automatic fraction separator which is controlled so that the temperature at the top of column 6 does not exceed 57.6° C.

After a temperature of 150° to 155° C has been attained at the temperature sensing device which is connected with control element 11, 1.74 mols of hexamethyldisiloxane are pumped through conduit 1 by control element 11 by means of pump 10. An average of 2.66 mols per hour of dimethyldichlorosilane is added through conduit 3 and 3 liters per hour of gaseous hydrogen chloride are pumped through conduit 5 into reaction column 6. By connecting or disconnecting pump 10, the temperature sensing device which is connected with control element 11 maintains a constant temperature between 150° and 155° C.

An hourly average of 3.31 mols of trimethyldichlorosilane is recovered from conduit 2.

The following table 7 shows the distribution of the product in percent obtained from conduit 4.

TABLE 7

| Components | Percent |
|---|---|
| $(CH_3)_2SiCl_2$ | 3.2 |
| $Cl(CH_3)_2SiOSi(CH_3)_2Cl$ | 22.7 |
| $Cl(CH_3)_2SiOSi(CH_3)_2OSi(CH_3)_2Cl$ | 45.8 |
| $Cl(CH_3)_2SiO[Si(CH_3)_2O]_2Si(CH_3)_2Cl$ | 15.9 |
| $Cl(CH_3)_2SiO[Si(CH_3)_2O]_3Si(CH_3)_2Cl$ | 4.6 |
| $Cl(CH_3)_2SiO[Si(CH_3)_2O]_4Si(CH_3)_2Cl$ | 1.6 |
| $Cl(CH_3)_2SiO[Si(CH_3)_2O]_5Si(CH_3)_2Cl$ | 0.5 |
| $Cl(CH_3)_2SiO[Si(CH_3)_2O]_6Si(CH_3)_2Cl$ | 0.2 |
| $Cl(CH_3)_2SiOSi(CH_3)_3$ | 0.6 |
| $Cl(CH_3)_2SiOSi(CH_3)_2OSi(CH_3)_3$ | 1.9 |
| $Cl(CH_3)_2SiO[Si(CH_3)_2O]_2Si(CH_3)_3$ | 0.9 |
| $Cl(CH_3)_2SiO[Si(CH_3)_2O]_3Si(CH_3)_3$ | 0.3 |
| $Cl(CH_3)_2SiO[Si(CH_3)_2O]_4Si(CH_3)_3$ | 0.1 |
| $(CH_3)_3SiOSi(CH_3)_2OSi(CH_3)_3$ | 0.2 |
| $(CH_3)_3SiO[Si(CH_3)_2O]_2Si(CH_3)_3$ | 0.4 |
| $(CH_3)_3SiO[Si(CH_3)_2O]_3Si(CH_3)_3$ | 0.1 |
| $[(CH_3)_2SiO]_3$ | 0.2 |
| $[(CH_3)_2SiO]_4$ | 0.3 |
| $[(CH_3)_2SiO]_5$ | 0.2 |

EXAMPLE 17

Reaction column 6 which is identical with that described in Example 15 and which contains activated charcoal and Raschig rings is employed in this Example.

The forced circulation evaporator 9 is filled with tetramethyldisiloxane and heated to ebullition under reflux. Dimethyldichlorosilane is introduced through conduit 1 and gaseous hydrogen chloride is conveyed through conduit 5 to the reaction column 6 until the temperature at the temperature sensing device has increased to between 130° and 135° C. The dimethylchlorosilane thus formed is withdrawn through conduit 2 via the automatic fraction separator which is controlled so that the temperature at the top of the column 6 does not exceed 36° C.

About 0.49 mols per hour of dimethyldichlorosilane is pumped by pump 10 through conduit 1 into the reaction column 6; while an hourly average of 1.1 mols of tetramethyldisiloxane is pumped through conduit 3 and 3 liters per hour of gaseous hydrogen chloride are pumped into reaction column 6 through conduit 5. The temperature sensing device which is connected to the control element 11 maintains the temperature between 130° and 135° C by connecting or disconnecting the pump 10 as required.

An hourly average of 0.97 mol of dimethylchlorosilane is obtained from conduit 2.

Table 8 shows distribution of the product in percent exiting from conduit 4 as determined by a gas chromatogram.

TABLE 8

| Components | Percent |
|---|---|
| $(CH_3)_2HSiOSi(CH_3)_2H$ | 6.0 |
| $(CH_3)_2HSiOSi(CH_3)_2OSiH(CH_3)_2$ | 27.8 |
| $(CH_3)_2HSiO[Si(CH_3)_2O]_2Si(CH_3)_2H$ | 48.2 |
| $(CH_3)_2HSiO[Si(CH_3)_2O]_3Si(CH_3)_2H$ | 5.7 |
| $(CH_3)_2SiO[Si(CH_3)_2O]_4Si(CH_3)_2H$ | 2.2 |
| $(CH_3)_2HSiO[Si(CH_3)_2O]_5Si(CH_3)_2H$ | 0.9 |
| $Cl(CH_3)_2SiOSi(CH_3)_2Cl$ | 0.6 |
| $Cl(CH_3)_2SiOSi(CH_3)_2OSi(CH_3)_2Cl$ | 0.3 |
| $Cl(CH_3)_2SiO[Si(CH_3)_2O]_2Si(CH_3)_2Cl$ | 0.1 |
| $[(CH_3)_2O]_3$ | 1.4 |
| $[(CH_3)_2O]_4$ | 5.1 |
| $[(CH_3)_2O]_5$ | 1.1 |
| $Cl(CH_3)_2SiOSi(CH_3)_2OSi(CH_3)_2H$ | 0.3 |
| $Cl(CH_3)_2SiO[Si(CH_3)_2O]_2Si(CH_3)_2H$ | 0.1 |

EXAMPLE 18

Tetramethyldisiloxane is added to the forced circulation evaporator 9 of the reaction column 6 containing activated charcoal and Raschig rings in accordance with the procedure described in Example 15. The tetramethyldisiloxane is heated to ebullition under reflux. Phenyltrichlorosilane is introduced into reaction column 6 through conduit 1 and gaseous hydrogen chloride is conveyed through conduit 5 until a temperature of from 130° to 135° C is attained at the temperature sensing device which is connected to control element 11. The dimethylchlorosilane thus formed is withdrawn through conduit 2 via the automatic fraction separator which is controlled so that the temperature at the top of column 6 never exceeds 36° C.

About 0.62 mol per hour of phenyltrichlorosilane is pumped via pump 10 which is regulated by the control element 11 through conduit 1 to the reaction column 6; while an hourly average of 1.86 mols of tetramethyldichlorosiloxane is pumped through conduit 3 and 3 liters per hour of gaseous hydrogen chloride are pumped into the reaction column 6 through conduit 5. A temperature between 135° and 140° C is maintained by the temperature sensing device connected to the control element 11 which connects or disconnects the pump 10 as required.

An average of 1.82 mols per hour of dimethylchlorosilane is recovered from conduit 2.

Table 9 shows the distribution of the product in percent obtained from conduit 4 as determined by a gas chromatogram.

TABLE 9

| Components | Percent |
|---|---|
| $C_6H_5Si[OSi(CH_3)_2H]_3$ | 81.1 |
| $C_6H_5[H(CH_3)_2SiO]_2SiOSi[(CH_3)_2SiOH]_2C_6H_5$ | 5.2 |
| $H(CH_3)_2SiOSi(CH_3)_2H$ | 11.2 |
| $C_6H_5Si[OSi(CH_3)_2]_2Cl$ | 2.2 |
| $HSi(CH_3)_2O[(CH_3)_2SiO]_dSi(CH_3)_2H$ | trace |
| d = 1 or 2 | |

EXAMPLE 19

The forced circulation evaporator 9 of the reaction column 6 which is filled with activated charcoal and Raschig rings in accordance with Example 15, is filled with hexamethyldisiloxane. The hexamethyldisiloxane is heated to ebullition under reflux. Phenyltrichlorosilane is introduced through conduit 1 and gaseous hydrogen chloride is conveyed through conduit 5 to the reaction column 6 until a temperature of 150° to 155° C is attained at the temperature sensing device connected to the control element 11. The trimethylchlorosilane thus formed is withdrawn through conduit 2 via the automatic fraction separator which is controlled so that the temperature at the top of column 6 does not exceed 57.4° C.

About 0.95 mol per hour of phenyltrichlorosilane is pumped through conduit 1 with the aid of pump 10 which is regulated by control element 11. An hourly average of 2.36 mols of hexamethyldisiloxane is pumped through conduit 3 and 3 liters per hour of gaseous hydrogen chloride are pumped into reaction column 6 through conduit 5. The temperature at the temperature sensing device is maintained in the range of from 150° to 155° C by control element 11 which connects or disconnects the pump 10 as required.

An hourly average of 2.78 mols of trimethylchlorosilane is obtained from conduit 2.

Table 10 shows the distribution of product in percent obtained from conduit 4 as indicated by the gas chromatogram.

TABLE 10

| Components | Percent |
|---|---|
| (CH$_3$)$_3$SiOSi(CH$_3$)$_3$ | 22.1 |
| C$_6$H$_5$Si[OSi(CH$_3$)$_3$]$_3$ | 52.9 |
| C$_6$H$_5$[(CH$_3$)$_3$SiO]$_2$SiOSi[OSi(CH$_3$)$_3$]$_2$C$_6$H$_5$ | 18.4 |
| C$_6$H$_5$Si[OSi(CH$_3$)$_3$]$_2$OSiC$_6$H$_5$[OSi(CH$_3$)$_3$] | 4.9 |
| O—SiC$_6$H$_5$[OSi(CH$_3$)$_3$]$_2$ | |
| C$_6$H$_5$Si[OSi(CH$_3$)$_3$]$_2$ OSiC$_6$H$_5$[OSi(CH$_3$)$_3$]$_2$OSi[OSi(CH$_3$)$_3$]$_2$ | 1.1 |
| C$_6$H$_5$SiCl[OSi(CH$_3$)$_3$]$_2$ | 0.4 |
| [C$_6$H$_5$[(CH$_3$)$_3$SiO]SiO]$_d$ | trace |
| d = 3 or 4 | |

EXAMPLE 20

Vinylmethyldichlorosilane is placed in the forced circulation evaporator 9 of reaction column 6 containing activated charcoal and Raschig rings as described in Example 15. The vinylmethyldichlorosilane is heated to ebullition under reflux. Hexamethyldisiloxane is introduced through conduit 1 and gaseous hydrogen chloride is introduced through conduit 5 to the reaction column 6 until a temperature of 130° C to 133° C has been attained at the temperature sensing device connected to control element 11. The trimethylchlorosilane so formed is removed through conduit 2 via the automatic fraction separator which is controlled so that the temperature at the top of column 6 does not exceed 57.5° C.

About 0.72 mol of hexamethyldisiloxane is introduced through conduit 1, with the flow being regulated by the control element 11 via the pump 10. An average of about 1.49 mols per hour of vinylmethyldichlorosilane is pumped through conduit 3 and 3 liters per hour of gaseous hydrogen chloride are pumped into reaction column 6 through conduit 5. The control element 11 maintains a temperature in the range of 130° to 133° C by connecting or disconnecting the pump 10 as required.

An hourly rate of about 1.47 mols of trimethylchlorosilane is obtained from conduit 2.

Table 11 shows the various components present in the product obtained from conduit 4 as determined by gas chromatogram.

TABLE 11

| Components | Percent |
|---|---|
| (CH$_3$)C$_2$H$_3$SiCl$_2$ | 21.0 |
| Cl(CH$_3$)C$_2$H$_3$SiOSiC$_2$H$_3$(CH$_3$)Cl | 57.2 |
| Cl(CH$_3$)C$_2$H$_3$SiOSiC$_2$H$_3$(CH$_3$)OSiC$_2$H$_3$(CH$_3$)Cl | 13.5 |
| Cl(CH$_3$)C$_2$H$_3$SiO[SiC$_2$H$_3$(CH$_3$)O]$_2$SiC$_2$H$_3$(CH$_3$)Cl | 6.4 |
| Cl(CH$_3$)C$_2$H$_3$SiO[SiC$_2$H$_3$(CH$_3$)O]$_3$SiC$_2$H$_3$(CH$_3$)Cl | 1.7 |
| (CH$_3$)$_3$SiOSiC$_2$H$_3$(CH$_3$)Cl | trace |

What is claimed is:

1. An improved process for equilibrating organosiloxanes by reacting organosiloxanes with chlorosilanes in the presence of a catalyst, the improvement which consists essentially of conducting the equilibration reaction in the presence of a catalyst selected from the class consisting of (a) activated charcoal and (b) activated charcoal and an inorganic acid.

2. The improved process of claim 1, wherein the organosiloxanes are cyclic siloxanes having the formula:

$$(R_2SiO)_n$$

in which R may be the same or different and is selected from the class consisting of monovalent hydrocarbon radicals, halogenated hydrocarbon radicals and hydrogen with the provision that no more than one hydrogen atom is bonded to each silicon atom; and $n$ is a whole number of from 3 to 10.

3. The improved process of claim 1, wherein the organosiloxanes have the general formula:

$$R_3SiO(R_2SiO)_mSiR_3,$$

in which R may be same or different and is selected from the class consisting of monovalent hydrocarbon radicals, halogenated hydrocarbon radicals and hydrogen with the provision that no more than one hydrogen atom is bonded to each silicon atom, and $m$ is 0 or a whole number.

4. The improved process of claim 3, wherein the chlorosilanes are represented by the formula:

$$R_{x'}SiCl_{4-x'}$$

in which R is the same or different and is selected from the class consisting of monovalent hydrocarbon radicals, halogenated hydrocarbon radicals and hydrogen, with the provision that no more than one hydrogen atom is bonded to each silicon atom; and $x'$ is 0, 1 or 2.

5. The improved process of claim 4, wherein the equilibration is conducted as a continuous process in a reaction column containing a stratum of activated carbon.

6. The improved process of claim 5, wherein the chlorosilane is introduced into the upper portion of the activated charcoal stratum and the organosiloxane having the formula:

$$R_3SiO(R_2SiO)_{m'}SiR_3$$

in which R is selected from the class consisting of monovalent hydrocarbon radicals, halogenated hydrocarbon radicals and hydrogen, with the provision that no more than one hydrogen atom is bonded to each silicon atom and $m''$ is 0, 1 or 2; is introduced below the activated charcoal stratum and thereafter the reaction components and reaction products in the reaction column are heated to ebullition.

7. The improved process of claim 6, wherein the organosiloxane is introduced in the lower portion of the activated charcoal stratum.

8. The improved process of claim 5, wherein an organosiloxane of the formula:

$$R_3SiO(R_2SiO)_{m'''}SiR_3$$

in which R is selected from the class consisting of monovalent hydrocarbon radicals, halogenated hydrocarbon radicals and hydrogen, with the provision that no more than one hydrogen atom is bonded to each silicon atom and $m'''$ is 0 or a whole number of from 1 to 25, is introduced into the upper portion of the activated charcoal stratum while the chlorosilane is introduced into the lower portion of the activated charcoal layer, and thereafter the reaction components and reaction products are heated to ebullition.

9. The improved process of claim 8, wherein the chlorosilane is introduced below the activated charcoal stratum.

10. The improved process of claim 6, wherein the addition of the organosiloxane to the reaction column is controlled by a device which is regulated by the prevailing temperature in the lower one-third of the reaction column.

11. The improved process of claim 8, wherein the addition of the chlorosilane to the reaction column is controlled by a device which is regulated by the prevailing temperature in the lower one-third of the reaction column.

* * * * *